US00PP27662P3

(12) United States Plant Patent
Jury

(10) Patent No.: US PP27,662 P3
(45) Date of Patent: Feb. 14, 2017

(54) ***DAPHNE* PLANT NAMED 'DAPJUR01'**

(50) Latin Name: *Daphne odora×bholua*
Varietal Denomination: DAPJUR01

(71) Applicant: Mark Jury, Waitara (NZ)

(72) Inventor: Mark Jury, Waitara (NZ)

( * ) Notice: Subject to any disclaimer, the term of this patent is extended or adjusted under 35 U.S.C. 154(b) by 102 days.

(21) Appl. No.: 14/545,464

(22) Filed: May 7, 2015

(65) Prior Publication Data

US 2016/0330889 P1 Nov. 10, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Daphne* cultivar named 'DAPJUR01' is disclosed, characterized by an abundance of large, highly fragrant flowers. Plants are bushy and produce unique, unusually long racemes of flowers. Additionally the new variety is sun tolerant. The new variety is a *Daphne*, normally produced as an outdoor garden or container plant.

2 Drawing Sheets

Figure 1:
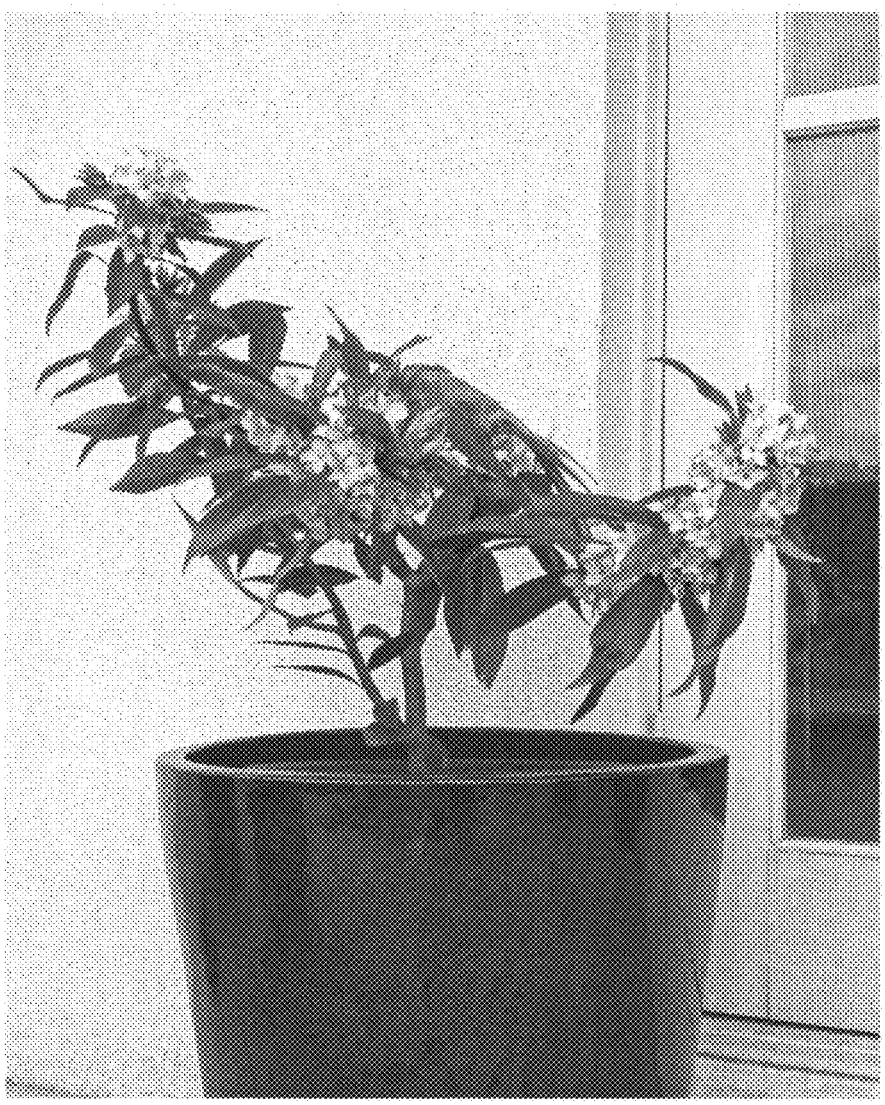

Latin name of the genus and species: *Daphne odora× bholua*.

Variety denomination: 'DAPJUR01'.

BACKGROUND OF THE INVENTION

The new *Daphne* cultivar is a product of a planned breeding program conducted by the inventor, Mark Jury. The new variety resulted from a crossing performed in 2004 in North Taranaki, Nth Is, New Zealand. The seed parent is the unpatented variety, *Daphne odora* 'Grace Stewart'. The pollen parent is an unnamed, unpatented variety *Daphne bholua*. The new variety was first selected in 2010, by the inventor, Mark Jury at a commercial nursery in North Taranaki, New Zealand.

Asexual reproduction of the new cultivar was performed by vegetative cuttings. This was first performed at a research greenhouse in North Taranaki, New Zealand in 2011 and has shown that the unique features of this cultivar are stable and reproduced true to type in more than 10 successive generations.

First public access to the variety occurred during June 2014, by a source receiving material from the inventor. Prior to this, all plant material was confidentially held by the inventor, or a party receiving plant material directly from the inventor. Any party obtaining plant material from the inventor also prevented public access to plants of the new variety. Plant Breeder's rights have been applied for in Europe, Apr. 22, 2015, having CPVO application number 2015/0907.

SUMMARY OF THE INVENTION

The cultivar 'DAPJUR01' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DAPJUR01' These characteristics in combination distinguish 'DAPJUR01' as a new and distinct *Daphne* cultivar:

1. Large flowers.
2. Unique flowering configuration, with flowers forming a spike like raceme, instead of a terminal cluster head of flowers, which is typical of *Daphne*.
3. Highly fragrant flowers.
4. Suitability for both container and garden plantings.
5. Bushy plant habit.
6. Sun tolerance.

PARENT COMPARISON

Plants of the new cultivar 'DAPJUR01' are similar to plants of the seed parent in most horticultural characteristics, however, plants of the new cultivar 'DAPJUR01' differ in the following;

1. The new variety has a much larger flower.
2. The new variety is more floriferous.
3. The new variety has a lighter color flower.

Plants of the new cultivar 'DAPJUR01' are similar to plants of the pollen parent in most horticultural characteristics, however, plants of the new cultivar 'DAPJUR01' differ in the following;

1. Plants of 'DAPJUR01' are more compact in habit than the pollen parent.
2. Plants of 'DAPJUR01' produce a larger flower.
3. The new variety produces a deeper colored flower.

COMMERCIAL COMPARISON

Plants of the new cultivar 'DAPJUR01' are comparable to the unpatented commercial variety *Daphne odora* 'Alba'. The two *Daphne* varieties are similar in most horticultural characteristics; however, the new variety 'DAPJUR01' differs in the following:

1. The new variety has larger flowers.
2. Flowers of the new variety are light pink. The comparator's flowers are white.

3. New variety has a lighter leaf color.
4. The new variety is sun tolerant. The comparator is not known to be sun tolerant.
5. The new variety has a longer flowering period.

BRIEF DESCRIPTION OF THE PHOTOGRAPHS

The accompanying photograph in FIG. 1 illustrates in full color a typical plant of 'DAPJUR01' grown in a nursery. Age of the plant photographed is approximately 2 years old.

Figure 2:
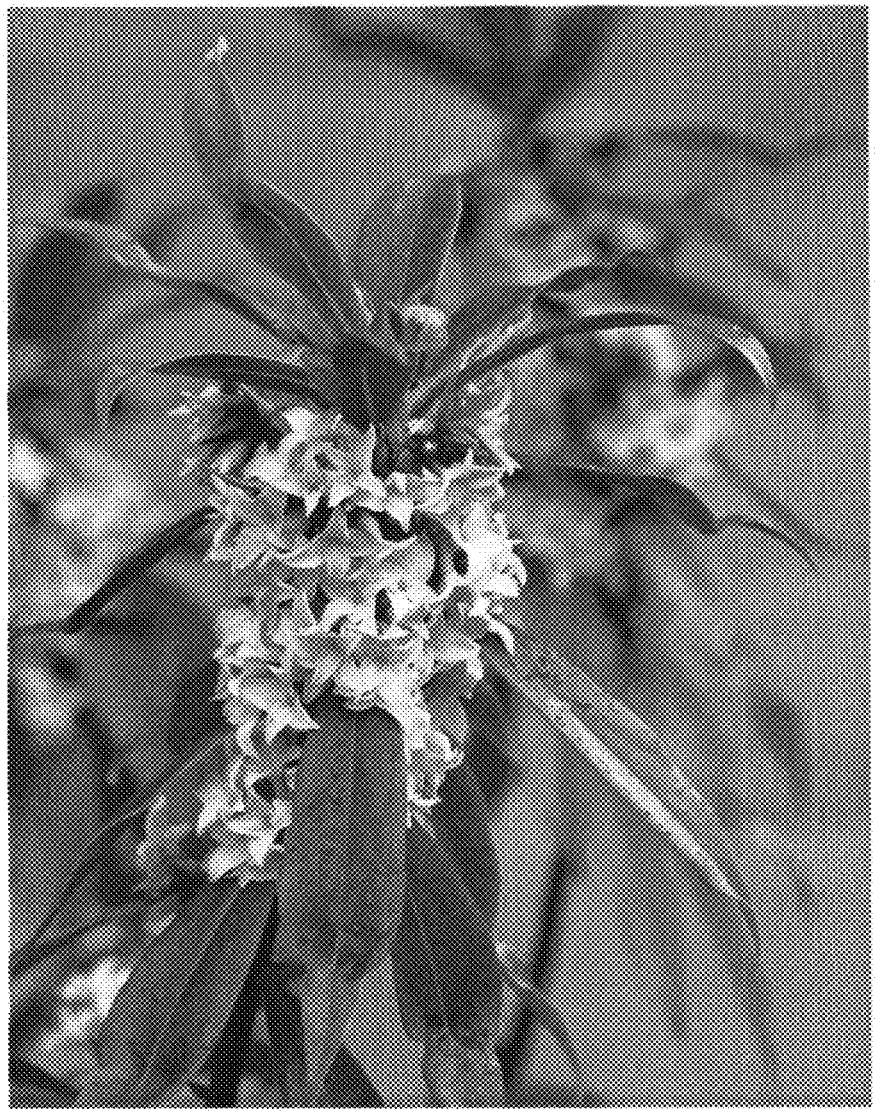

FIG. 2 illustrates a close up of the inflorescence and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'DAPJUR01' plants grown outdoors during the Spring and Summer in North Taranaki, New Zealand. The growing temperature ranged from 12° C. to 30° C. during the day and from 8° C. to 15° C. during the night. General light conditions are bright, normal sunlight. Measurements and numerical values represent averages of typical plant types.

Botanical classification: *Daphne* 'DAPJUR01'.

PROPAGATION

Time to rooting: Approximately 4 to 8 weeks at approximately 20° C. to 30° C. from semi-hardwood cuttings.

Root description: Fine, fibrous young roots. Older roots becoming woody.

PLANT

Age of plant described: Approximately 2 years.

Growth habit: Strong, bushy, compact deciduous shrub.

Height: Mature plant height approximately 100 to 120 cm.

Plant spread: 100 cm.

Growth rate: Rapid for Genus.

Branching characteristics: Above average branching for Genus.

Characteristics of primary lateral branches:

*Quantity of primary lateral branches.*—5.

Diameter of lateral branches: Approximately 0.5 cm.

Lateral branch strength: Very strong, with some flexibility.

Lateral branch color:

*Young branches.*—Near RHS Yellow-Green 144A.

*Mature branches (more than 3 years).*—Near RHS Grey-Brown N199A.

Other stem or plant characteristics: No pubescence or lenticels observed. Texture moderately rough.

FOLIAGE

Leaf:

*Type.*—Simple.

*Arrangement.*—Alternate.

*Average length.*—Approximately 10.0 cm.

*Average width.*—Approximately 3.0 cm.

*Shape of blade.*—Elliptic.

*Apex.*—Acute, or occasionally mucronate.

*Base.*—Tapered.

*Attachment.*—Sessile.

*Margin.*—Entire.

*Texture of top surface.*—Smooth.

*Texture of bottom surface.*—Smooth.

*Leaf internode length.*—Approximately 0.9 to 1.5 cm.

*Color.*—Young foliage upper side: Near RHS Yellow-Green 144A. Young foliage under side: Near RHS Yellow-Green 144B. Mature foliage upper side: Near RHS Green 138A. Mature foliage under side: Near RHS Green 138A.

*Venation.*—Type: Pinnate. Venation color upper side: Near RHS Yellow-Green N144A. Venation color under side: Near RHS Yellow-Green N144B.

Petiole: Not present, sessile.

FLOWER

Natural flowering season: Autumn until Spring.

Inflorescence and flower type and habit: Raceme. Single trumpet shaped flowers composed of petaloid sepals. Corolla not present.

Inflorescence:

*Diameter.*—Approximately 6.0 cm.

*Length.*—Average 12.0 cm.

Individual flower:

*Diameter.*—Approximately 3.0 to 4.0 cm.

*Depth.*—Approximately 5.0 cm.

*Quantity of flowers per inflorescence.*—Average range 16 to 24.

Persistent or self-cleaning: Self-cleaning.

Fragrance: Very strong sweet scent.

Bud:

*Shape.*—Conical operculum.

*Length.*—1 cm.

*Diameter.*—0.3 cm.

*Color.*—RHS Purple 77B.

Petaloid sepals:

*Quantity.*—4.

*Length.*—Approximately 1.0 to 2.0 cm.

*Width.*—Approximately 0.6 to 0.9 cm.

*Apex.*—Acute.

*Shape of petal.*—Ovate.

*Petal margin.*—Entire.

*Petal arrangement.*—Whorled, not overlapping.

*Petal texture.*—Smooth.

*Color.*—Upper surface at first opening: Near RHS Violet-Blue 92D, margin Red-Purple 72B. Under surface at maturity: Near RHS Near RHS Violet-Blue 92D, margin Red-Purple 72B.

Pedicels:

*Length.*—1.0 cm.

*Diameter.*—0.2 cm.

*Color.*—RHS Yellow-green 144B.

*Texture.*—Pubescent.

REPRODUCTIVE ORGANS

Stamens:

*Number* (*per flower*).—4.

*Filament length.*—0.1 cm.

*Anthers.*—Shape: Conical. Length: 0.05 mm. Color: RHS White N155D.

Pollen: Pollen not produced.

Pistils:

*Quantity per flower.*—1.

*Length.*—0.2 cm.

*Styles.*—Length: Less than 0.1 cm. Color: RHS White N155D.

OTHER CHARACTERISTICS

Seeds and fruits: Not produced.

Disease/pest resistance: Neither resistance nor susceptibility to the normal diseases and pests of *Daphne* has been observed.

Temperature tolerance: Tolerates temperatures from approximately −15° C. to 38° C.

What is claimed is:

1. A new and distinct cultivar of *Daphne* plant named 'DAPJUR01' as herein illustrated and described.

* * * * *